United States Patent
Ogino et al.

(10) Patent No.: US 7,153,945 B2
(45) Date of Patent: Dec. 26, 2006

(54) PEPTIDE, NOVEL ADSORBENT, ADSORPTION UNIT AND ADSORPTION METHOD

(75) Inventors: Eiji Ogino, Settsu (JP); Takehiro Nishimoto, Settsu (JP); Michio Nomura, Settsu (JP); Shigeo Furuyoshi, Settsu (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 10/489,202

(22) PCT Filed: Sep. 18, 2002

(86) PCT No.: PCT/JP02/09572

§ 371 (c)(1),
(2), (4) Date: Sep. 7, 2004

(87) PCT Pub. No.: WO03/025011

PCT Pub. Date: Mar. 27, 2003

(65) Prior Publication Data

US 2005/0038228 A1 Feb. 17, 2005

(30) Foreign Application Priority Data

Sep. 18, 2001 (JP) ............................. 2001-283583

(51) Int. Cl.
*A61K 39/00* (2006.01)
(52) U.S. Cl. .................................... 530/412; 424/140.1
(58) Field of Classification Search ............... 530/413; 424/140.1, 140
See application file for complete search history.

(56) References Cited

U.S. PATENT DOCUMENTS

| 4,956,296 | A | | 9/1990 | Fahnestock | |
|---|---|---|---|---|---|
| 4,977,247 | A | | 12/1990 | Fahnestock et al. | |
| 5,290,690 | A | * | 3/1994 | Mrabet et al. | 435/189 |
| 5,312,901 | A | | 5/1994 | Fahnestock | |
| 6,133,431 | A | * | 10/2000 | Yasuda et al. | 530/413 |
| 6,277,615 | B1 | * | 8/2001 | Varghese et al. | 435/200 |
| 6,677,432 | B1 | * | 1/2004 | Oppermann et al. | 530/350 |

FOREIGN PATENT DOCUMENTS

| EP | 1 013 669 A2 | 6/2000 |
|---|---|---|
| JP | 02764021 | 11/1999 |
| WO | WO 97/26930 | 7/1997 |
| WO | WO 98/42392 | 10/1998 |

OTHER PUBLICATIONS

Sauer-Eriksson, A. E., et al., "*Crystal structure of the C2 fragment of streptococcal protein G in complex with Fc domain of human IgG*", Structure 3:265-278 (1995).

* cited by examiner

*Primary Examiner*—Christina Chan
*Assistant Examiner*—Yunsoo Kim
(74) *Attorney, Agent, or Firm*—Kenyon & Kenyon LLP

(57) ABSTRACT

The present invention provides an adsorbent, adsorption unit, and an adsorption method which make it possible to selectively adsorb an immunoglobulin and/or an immune complex present in a body fluid (for example, blood, plasma, etc.) efficiently without pretreating the body fluid. By immobilizing a compound having binding activity for an immunoglobulin and/or an immune complex on a water-insoluble carrier, an adsorbent having remarkably excellent adsorption capacity may be obtained.

8 Claims, 2 Drawing Sheets

SEQUENCE LISTING

```
<160> NUMBER OF SEQ ID NOS: 19

<210> SEQ ID NO 1
<211> LENGTH: 57
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: 32
<223> OTHER INFORMATION: Asn or Lys or Gln
<220> FEATURE:
<221> NAME/KEY: misc_feature
<222> LOCATION: 35
<223> OTHER INFORMATION: Thr or Asn
<220> FEATURE:
<221> NAME/KEY: misc_feature
<222> LOCATION: 40
<223> OTHER INFORMATION: Glu or Asp
<220> FEATURE:
<221> NAME/KEY: misc_feature
<222> LOCATION: 42
<223> OTHER INFORMATION: Leu or Val or Ile or Met

<400> SEQUENCE: 1

Thr Thr Tyr Lys Leu Val Ile Asn Gly Lys Thr Leu Lys Gly Glu Thr
 1               5                  10                  15

Thr Thr Lys Ala Val Asp Ala Glu Thr Ala Glu Arg Ala Phe Arg Xaa
            20                  25                  30

Tyr Ala Xaa Asp Asn Gly Val Xaa Gly Xaa Trp Thr Tyr Asp Pro Ala
        35                  40                  45

Thr Lys Thr Phe Thr Val Thr Glu Cys
    50                  55

<210> SEQ ID NO 2
<211> LENGTH: 171
<212> TYPE: DNA
<213> ORGANISM: Artificial Sequence
<220> FEATURE:
<223> OTHER INFORMATION: Description of Artificial Sequence: Synthetic
      DNA
```

```
<220> FEATURE:
<221> NAME/KEY: misc_feature
<222> LOCATION: 94
<223> OTHER INFORMATION: a if location 96 is c, t, aor g; c if location
     96 is a or g
<220> FEATURE:
<221> NAME/KEY: misc_feature
<222> LOCATION: 96
<223> OTHER INFORMATION: c, t, a or g is location 94 is a; or a or g if
     location 94 is c
<220> FEATURE:
<221> NAME/KEY: misc_feature
<222> LOCATION: 104
<223> OTHER INFORMATION: c if location 105 is a, g, c or t; or a if
     location 105 is c or t
<220> FEATURE:
<221> NAME/KEY: misc_feature
<222> LOCATION: 105
<223> OTHER INFORMATION: a, g, c or t if location 104 is c; or c or t if
     location 104 is a
<220> FEATURE:
<221> NAME/KEY: misc_feature
<222> LOCATION: 120
<223> OTHER INFORMATION: a, g, c or t
<220> FEATURE:
<221> NAME/KEY: misc_feature
<222> LOCATION: 124
<223> OTHER INFORMATION: c, t, g or a if location 126 is a or 9; or c, g
     or a if location 126 is c or t
<220> FEATURE:
<221> NAME/KEY: misc_feature
<222> LOCATION: 126
<223> OTHER INFORMATION: c or t if location 124 is g or a; or a or g if
     location 124 is c, t, g or a

<400> SEQUENCE: 2 acc acc tat aaa ctg gtt atc aac ggt aaa acc ctg aaa ggt gaa acc      48
Thr Thr Tyr Lys Leu Val Ile Asn Gly Lys Thr Leu Lys Gly Glu Thr
 1               5                  10                  15 acc acc aag gct gtt gac gct gaa acc gct gag cgc gca ttt cgg nan      96
Thr Thr Lys Ala Val Asp Ala Glu Thr Ala Glu Arg Ala Phe Arg Xaa
             20                  25                  30 tat gct ann gac aac ggt gtc gan ggt ntn tgg acc tat gac ccc gct     144
Tyr Ala Xaa Asp Asn Gly Val Xaa Gly Xaa Trp Thr Tyr Asp Pro Ala
         35                  40                  45 acc aaa acc ttt acc gtt acc gaa tgc                                 171
Thr Lys Thr Phe Thr Val Thr Glu Cys
     50                  55

<210> SEQ ID NO 3
<211> LENGTH: 55
<212> TYPE: PRT
<213> ORGANISM: Streptococcus sp. G148

<400> SEQUENCE: 3

Thr Tyr Lys Leu Ile Leu Asn Gly Lys Thr Leu Lys Gly Glu Thr Thr
 1               5                  10                  15

Thr Glu Ala Val Asp Ala Ala Thr Ala Glu Lys Val Phe Lys Gln Tyr
             20                  25                  30

Ala Asn Asp Asn Gly Val Asp Gly Glu Trp Thr Tyr Asp Asp Ala Thr
         35                  40                  45

Lys Thr Phe Thr Val Thr Glu
     50                  55

<210> SEQ ID NO 4
<211> LENGTH: 55
<212> TYPE: PRT
<213> ORGANISM: Streptococcus sp. G148
```

-continued

```
<400> SEQUENCE: 4

Thr Tyr Lys Leu Val Ile Asn Gly Lys Thr Leu Lys Gly Glu Thr Thr
 1               5                  10                  15

Thr Glu Ala Val Asp Ala Ala Thr Ala Glu Lys Val Phe Lys Gln Tyr
             20                  25                  30

Ala Asp Asp Asn Gly Val Asp Gly Glu Trp Thr Tyr Asp Asp Ala Thr
         35                  40                  45

Lys Thr Phe Thr Val Thr Glu
         50                  55

<210> SEQ ID NO 5
<211> LENGTH: 55
<212> TYPE: PRT
<213> ORGANISM: Streptococcus sp. G148

<400> SEQUENCE: 5

Thr Tyr Lys Leu Val Ile Asn Gly Lys Thr Leu Lys Gly Glu Thr Thr
 1               5                  10                  15

Thr Lys Ala Val Asp Ala Glu Thr Ala Glu Lys Ala Phe Lys Gln Tyr
             20                  25                  30

Ala Asn Asp Asn Gly Val Asp Gly Val Trp Thr Tyr Asp Asp Ala Thr
         35                  40                  45

Lys Thr Phe Thr Val Thr Glu
         50                  55

<210> SEQ ID NO 6
<211> LENGTH: 56
<212> TYPE: PRT
<213> ORGANISM: Artificial Sequence
<220> FEATURE:
<223> OTHER INFORMATION: Description of Artificial Sequence: Synthetic
      C3 domain

<400> SEQUENCE: 6

Thr Thr Tyr Lys Leu Val Ile Asn Gly Lys Thr Leu Lys Gly Glu Thr
 1               5                  10                  15

Thr Thr Lys Ala Val Asp Ala Glu Thr Ala Glu Lys Ala Phe Lys Gln
             20                  25                  30

Tyr Ala Asn Asp Asn Gly Val Asp Gly Val Trp Thr Tyr Asp Asp Ala
         35                  40                  45

Thr Lys Thr Phe Thr Val Thr Glu
         50                  55

<210> SEQ ID NO 7
<211> LENGTH: 181
<212> TYPE: DNA
<213> ORGANISM: Artificial Sequence
<220> FEATURE:
<223> OTHER INFORMATION: Description of Artificial Sequence: Synthetic
      C3 domain DNA

<400> SEQUENCE: 7 catatg acc acc tat aaa ctg gtt atc aac ggt aaa acc ctg aaa ggt gaa acc   54
       Thr Thr Tyr Lys Leu Val Ile Asn Gly Lys Thr Leu Lys Gly Glu Thr
        1               5                  10                  15 acc acc aag gct gtt gac gct gaa acc gct gaa aaa gca ttt aaa cag          102
Thr Thr Lys Ala Val Asp Ala Glu Thr Ala Glu Lys Ala Phe Lys Gln
             20                  25                  30 tat gct aac gac aac ggt gtc gac ggt gtt tgg acc tat gac gac gct          150
Tyr Ala Asn Asp Asn Gly Val Asp Gly Val Trp Thr Tyr Asp Asp Ala
         35                  40                  45
```

```
acc aaa acc ttt acc gtt acc gaa taagctt                              181
Thr Lys Thr Phe Thr Val Thr Glu
    50                  55
```

<210> SEQ ID NO 8
<211> LENGTH: 58
<212> TYPE: PRT
<213> ORGANISM: Artificial Sequence
<220> FEATURE:
<223> OTHER INFORMATION: Description of Artificial Sequence: Synthetic
      C36

<400> SEQUENCE: 8

```
Met Thr Thr Tyr Lys Leu Val Ile Asn Gly Lys Thr Leu Lys Gly Glu
  1               5                  10                  15

Thr Thr Thr Lys Ala Val Asp Ala Glu Thr Ala Glu Arg Ala Phe Arg
             20                  25                  30

Gln Tyr Ala Thr Asp Asn Gly Val Glu Gly Met Trp Thr Tyr Asp Pro
         35                  40                  45

Ala Thr Lys Thr Phe Thr Val Thr Glu Cys
    50                  55
```

<210> SEQ ID NO 9
<211> LENGTH: 184
<212> TYPE: DNA
<213> ORGANISM: Artificial Sequence
<220> FEATURE:
<223> OTHER INFORMATION: Description of Artificial Sequence: Synthetic
      C36-DNA

<400> SEQUENCE: 9

```
cat atg acc acc tat aaa ctg gtt atc aac ggt aaa acc ctg aaa ggt gaa    51
    Met Thr Thr Tyr Lys Leu Val Ile Asn Gly Lys Thr Leu Lys Gly Glu
      1               5                  10                  15 acc acc acc aag gct gtt gac gct gaa acc gct gag cgc gca ttt cgg        99
Thr Thr Thr Lys Ala Val Asp Ala Glu Thr Ala Glu Arg Ala Phe Arg
             20                  25                  30 cag tat gct acg gac aac ggt gtc gaa ggt atg tgg acc tat gac ccc       147
Gln Tyr Ala Thr Asp Asn Gly Val Glu Gly Met Trp Thr Tyr Asp Pro
         35                  40                  45 gct acc aaa acc ttt acc gtt acc gaa tgc taagctt                       184
Ala Thr Lys Thr Phe Thr Val Thr Glu Cys
    50                  55
```

<210> SEQ ID NO 10
<211> LENGTH: 58
<212> TYPE: PRT
<213> ORGANISM: Artificial Sequence
<220> FEATURE:
<223> OTHER INFORMATION: Description of Artificial Sequence: Synthetic
      B04

<400> SEQUENCE: 10

```
Met Thr Thr Tyr Lys Leu Val Ile Asn Gly Lys Thr Leu Lys Gly Glu
  1               5                  10                  15

Thr Thr Thr Lys Ala Val Asp Ala Glu Thr Ala Glu Arg Ala Phe Arg
             20                  25                  30

Lys Tyr Ala Thr Asp Asn Gly Val Asp Gly Met Trp Thr Tyr Asp Pro
         35                  40                  45

Ala Thr Lys Thr Phe Thr Val Thr Glu Cys
    50                  55
```

-continued

```
<210> SEQ ID NO 11
<211> LENGTH: 58
<212> TYPE: PRT
<213> ORGANISM: Artificial Sequence
<220> FEATURE:
<223> OTHER INFORMATION: Description of Artificial Sequence: synthetic
      C04

<400> SEQUENCE: 11

Met Thr Thr Tyr Lys Leu Val Ile Asn Gly Lys Thr Leu Lys Gly Glu
 1               5                  10                  15

Thr Thr Thr Lys Ala Val Asp Ala Glu Thr Ala Glu Arg Ala Phe Arg
            20                  25                  30

Lys Tyr Ala Asn Asp Asn Gly Val Glu Gly Ile Trp Thr Tyr Asp Pro
        35                  40                  45

Ala Thr Lys Thr Phe Thr Val Thr Glu Cys
    50                  55

<210> SEQ ID NO 12
<211> LENGTH: 184
<212> TYPE: DNA
<213> ORGANISM: Artificial Sequence
<220> FEATURE:
<223> OTHER INFORMATION: Description of Artificial Sequence: Synthetic
      C04-DNA

<400> SEQUENCE: 12 cat atg acc acc tat aaa ctg gtt atc aac ggt aaa acc ctg aaa gga gaa      51
    Met Thr Thr Tyr Lys Leu Val Ile Asn Gly Lys Thr Leu Lys Gly Glu
     1               5                  10                  15 acc acc acc aag gct gtt gac gct gaa acc gct gaa aga gca ttt agg          99
Thr Thr Thr Lys Ala Val Asp Ala Glu Thr Ala Glu Arg Ala Phe Arg
            20                  25                  30 aag tat gct aac gac aac ggt gtc gaa ggt atc tgg acc tat gac ccc         147
Lys Tyr Ala Asn Asp Asn Gly Val Glu Gly Ile Trp Thr Tyr Asp Pro
        35                  40                  45 gct acc aaa acc ttt acc gtt acc gaa tgc taagctt                         184
Ala Thr Lys Thr Phe Thr Val Thr Glu Cys
    50                  55

<210> SEQ ID NO 13
<211> LENGTH: 58
<212> TYPE: PRT
<213> ORGANISM: Artificial Sequence
<220> FEATURE:
<223> OTHER INFORMATION: Description of Artificial Sequence: Synthetic
      C15

<400> SEQUENCE: 13

Met Thr Thr Tyr Lys Leu Val Ile Asn Gly Lys Thr Leu Lys Gly Glu
 1               5                  10                  15

Thr Thr Thr Lys Ala Val Asp Ala Glu Thr Ala Glu Arg Ala Phe Arg
            20                  25                  30

Gln Tyr Ala Asn Asp Asn Gly Val Glu Gly Leu Trp Thr Tyr Asp Pro
        35                  40                  45

Ala Thr Lys Thr Phe Thr Val Thr Glu Cys
    50                  55

<210> SEQ ID NO 14
<211> LENGTH: 184
<212> TYPE: DNA
<213> ORGANISM: Artificial Sequence
<220> FEATURE:
<223> OTHER INFORMATION: Description of Artificial Sequence: Synthetic
```

C15-DNA

<400> SEQUENCE: 14

```
cat atg acc acc tat aaa ctg gtt atc aac ggt aaa acc ctg aaa ggt gaa    51
    Met Thr Thr Tyr Lys Leu Val Ile Asn Gly Lys Thr Leu Lys Gly Glu
    1               5                   10                  15 acc acc acc aag gct gtt gac gct gaa acc gct gag cgc gca ttt cga        99
Thr Thr Thr Lys Ala Val Asp Ala Glu Thr Ala Glu Arg Ala Phe Arg
            20                  25                  30 cag tat gct aac gac aac ggt gtc gag ggt ctg tgg acc tat gac ccc       147
Gln Tyr Ala Asn Asp Asn Gly Val Glu Gly Leu Trp Thr Tyr Asp Pro
        35                  40                  45 gct acc aaa acc ttt acc gtt acc gaa tgc taagctt                       184
Ala Thr Lys Thr Phe Thr Val Thr Glu Cys
    50                  55
```

<210> SEQ ID NO 15
<211> LENGTH: 58
<212> TYPE: PRT
<213> ORGANISM: Artificial Sequence
<220> FEATURE:
<223> OTHER INFORMATION: Description of Artificial Sequence: Synthetic C24

<400> SEQUENCE: 15

```
Met Thr Thr Tyr Lys Leu Val Ile Asn Gly Lys Thr Leu Lys Gly Glu
1               5                   10                  15

Thr Thr Thr Lys Ala Val Asp Ala Glu Thr Ala Glu Arg Ala Phe Arg
            20                  25                  30

Lys Tyr Ala Asn Asp Asn Gly Val Asp Gly Met Trp Thr Tyr Asp Pro
        35                  40                  45

Ala Thr Lys Thr Phe Thr Val Thr Glu Cys
    50                  55
```

<210> SEQ ID NO 16
<211> LENGTH: 184
<212> TYPE: DNA
<213> ORGANISM: Artificial Sequence
<220> FEATURE:
<223> OTHER INFORMATION: Description of Artificial Sequence: Synthetic C24-DNA

<400> SEQUENCE: 16

```
cat atg acc acc tat aaa ctg gtt atc aac ggt aaa acc ctg aaa ggt gaa    51
    Met Thr Thr Tyr Lys Leu Val Ile Asn Gly Lys Thr Leu Lys Gly Glu
    1               5                   10                  15 acc acc acc aag gct gtt gac gct gaa acc gct gag cgc gca ttt cgg        99
Thr Thr Thr Lys Ala Val Asp Ala Glu Thr Ala Glu Arg Ala Phe Arg
            20                  25                  30 aag tat gct aac gac aac ggt gtc gac ggt atg tgg acc tat gac ccc       147
Lys Tyr Ala Asn Asp Asn Gly Val Asp Gly Met Trp Thr Tyr Asp Pro
        35                  40                  45 gct acc aaa acc ttt acc gtt acc gaa tgc taagctt                       184
Ala Thr Lys Thr Phe Thr Val Thr Glu Cys
    50                  55
```

<210> SEQ ID NO 17
<211> LENGTH: 57
<212> TYPE: PRT
<213> ORGANISM: Artificial Sequence
<220> FEATURE:
<223> OTHER INFORMATION: Description of Artificial Sequence: Synthetic MG56

```
<400> SEQUENCE: 17

Met Thr Thr Tyr Lys Leu Val Ile Asn Gly Lys Thr Leu Lys Gly Glu
 1               5                  10                  15

Thr Thr Thr Lys Ala Val Asp Ala Glu Thr Ala Glu Lys Ala Phe Lys
             20                  25                  30

Gln Tyr Ala Asn Asp Asn Gly Val Asp Gly Val Trp Thr Tyr Asp Asp
         35                  40                  45

Ala Thr Lys Thr Phe Thr Val Thr Glu
     50                  55

<210> SEQ ID NO 18
<211> LENGTH: 181
<212> TYPE: DNA
<213> ORGANISM: Artificial Sequence
<220> FEATURE:
<223> OTHER INFORMATION: Description of Artificial Sequence: Synthetic
      MG56-DNA

<400> SEQUENCE: 18 cat atg acc acc tat aaa ctg gtt atc aac ggt aaa acc ctg aaa ggt gaa      51
    Met Thr Thr Tyr Lys Leu Val Ile Asn Gly Lys Thr Leu Lys Gly Glu
     1               5                  10                  15 acc acc acc aag gct gtt gac gct gaa acc gct gaa aaa gca ttt aaa          99
Thr Thr Thr Lys Ala Val Asp Ala Glu Thr Ala Glu Lys Ala Phe Lys
             20                  25                  30 cag tat gct aac gac aac ggt gtc gac ggt gtt tgg acc tat gac gac         147
Gln Tyr Ala Asn Asp Asn Gly Val Asp Gly Val Trp Thr Tyr Asp Asp
         35                  40                  45 gct acc aaa acc ttt acc gtt acc gaa taagctt                             181
Ala Thr Lys Thr Phe Thr Val Thr Glu
     50                  55

<210> SEQ ID NO 19
<211> LENGTH: 27
<212> TYPE: PRT
<213> ORGANISM: Artificial Sequence
<220> FEATURE:
<223> OTHER INFORMATION: Description of Artificial Sequence: Synthetic
      beta1 adrenoceptor Position 197-222

<400> SEQUENCE: 19

His Trp Trp Arg Ala Glu Ser Asp Glu Ala Arg Arg Cys Tyr Asn Asp
 1               5                  10                  15

Pro Lys Cys Cys Asp Phe Val Thr Asn Arg Cys
             20                  25
```

PEPTIDE, NOVEL ADSORBENT, ADSORPTION UNIT AND ADSORPTION METHOD

This application is a 371 national phase application of PCT/JP02/09572 filed on 18 Sep. 2002, claiming priority to JP 2001-283583, filed on 18 Sep. 2001, the contents of which are incorporated herein by reference in their entirety.

TECHNICAL FIELD

The present invention relates to a novel peptide having affinities for an immunoglobulin and/or an immune complex, a nucleotide sequence coding for said peptide, a recombinant DNA having said nucleotide sequence, a microorganism comprising the DNA, and use of said microorganism or said DNA for the production of said peptide. The invention further relates to an adsorbent utilizing the affinities of said peptide for an immunoglobulin and/or an immune complex for selective adsorption of an immunoglobulin and/or an immune complex present in an aqueous solution, particularly in a body fluid (for example, blood, plasma, serum, etc.), an adsorption unit using said adsorbent, and a method for adsorbing an immunoglobulin and/or an immune complex.

BACKGROUND ART

A variety of proteins having affinities for an immunoglobulin and/or an immune complex are known and, among them, Protein A and Protein G have been particularly well studied. Both Protein A and Protein G have high affinities for an immunoglobulin and/or an immune complex, but whereas the affinity of Protein A for IgG3 is low, Protein G binds to IgG3 (Japanese Patent No. 02764021). Furthermore, the Protein G gene has been shown to have nucleotide sequences coding for 3 kinds of peptide binding to an immunoglobulin and/or an immune complex, which are called C1, C2 and C3, and the corresponding amino acid sequences are as shown under the SEQ ID NOs:3, 4 and 5 of the sequence listing (Japanese Patent No. 02764021). C1 (SEQ ID NO:3)

```
C1 (SEQ ID NO:3)
Thr Tyr Lys Leu Ile Leu Asn Gly Lys Thr

Leu Lys Gly Glu Thr Thr Thr Glu Ala Val

Asp Ala Ala Thr Ala Glu Lys Val Phe Lys

Gln Tyr Ala Asn Asp Asn Gly Val Asp Gly

Glu Trp Thr Tyr Asp Asp Ala Thr Lys Thr

Phe Thr Val Thr Glu

C2 (SEQ ID NO:4)
Thr Tyr Lys Leu Val Ile Asn Gly Lys Thr

Leu Lys Gly Glu Thr Thr Thr Glu Ala Val

Asp Ala Ala Thr Ala Glu Lys Val Phe Lys

Gln Tyr Ala Asn Asp Asn Gly Val Asp Gly

Glu Trp Thr Tyr Asp Asp Ala Thr Lys Thr

Phe Thr Val Thr Glu

C3 (SEQ ID NO:5)
```

```
-continued
Thr Tyr Lys Leu Val Ile Asn Gly Lys Thr

Leu Lys Gly Glu Thr Thr Thr Lys Ala Val

Asp Ala Glu Thr Ala Glu Lys Ala Phe Lys

Gln Tyr Ala Asn Asp Asn Gly Val Asp Gly

Val Trp Thr Tyr Asp Asp Ala Thr Lys Thr

Phe Thr Val Thr Glu
```

Furthermore, from an X-ray structure analysis of a complex composed of C2 and IgG (Fc), it has been clearly shown that Glu26, Lys27, Lys30, Gln31, Asn34, Asp39, Glu41 and Trp42 of C2 bond to Fc (Sauer-Eriksson AE, Kleywegt GJ, Uhlen M, Jones TA Crystal structure of the C2 fragment of streptococcal protein G in complex with the Fc domain of human IgG. Structure 1995 Mar. 15; 3 (3): 265–78).

One important possible application of a peptide or protein having affinities for an immunoglobulin and/or an immune complex is its application to an adsorbent for the purification, isolation and/or removal of an immunoglobulin and/or an immune complex. However, we found that said C1, C2 and C3 peptides are too thermally unstable to withstand the sterilization by autoclaving, and apt to sustain marked depressions in the binding activity by radiation sterilization.

SUMMARY OF THE INVENTION

In view of the above drawbacks, the present invention has objects to optimize amino acids inclusive of the Fc-binding amino acids (mentioned above) of a protein G-derived peptide, and to provide a novel peptide being not only at least equivalent to the original peptide (C3 mentioned above) in the affinities for an immunoglobulin and/or an immune complex but also stable against sterilization procedures; a nucleotide sequence coding for said peptide; a recombinant DNA having said nucleotide sequence; a microorganism comprising the DNA; use of said microorganism or said DNA for a production of said peptide; and furthermore, as an application example, an adsorbent for selective adsorption of an immunoglobulin and/or an immune complex present in aqueous solution, particularly in a body fluid (for example, blood, plasma, serum, etc.). Further objects of the invention are provision of an adsorption unit using said adsorbent and that of a method for adsorbing an immunoglobulin and/or an immune complex.

The inventors of the present invention constructed an extensive sequence of peptides using chemical and genetic-engineering techniques for accomplishing the above objects and have completed the present invention by applying various scientific techniques to characteristics of the resulting peptides.

The present invention, therefore, is related to:

a peptide having affinities for an immunoglobulin and/or an immune complex which comprises the amino acid sequence shown under the SEQ ID NO:1 of the sequence listing;

a nucleotide sequence which codes for at least one species of the amino acid sequence shown under the SEQ ID NO:1 of the sequence listing;

said nucleotide sequence
which comprises at least one species of the base sequence shown under the SEQ ID NO:2 of the sequence listing;
a recombinant DNA
which has one or more nucleotide sequences coding for the amino acid sequence shown under the SEQ ID NO: 1 of the sequence listing; and
a microorganism
which comprises at least one recombinant DNA having one or more nucleotide sequences coding for the amino acid sequence shown under the SEQ ID NO:1 of the sequence listing.

Furthermore, the present invention is related to:
an adsorbent for an immunoglobulin and/or an immune complex
which comprises a water-insoluble carrier having, as immobilized thereon, a peptide containing at least one species of the amino acid sequence shown under the SEQ ID NO:1 of the sequence listing and consisting of not more than 70 amino acid residues;
a method for adsorbing an immunoglobulin and/or an immune complex
which comprises bringing said adsorbent into contact with a body fluid containing an immunoglobulin and/or an immune complex; and
an adsorption unit
which comprises said absorbent filled in a container having a liquid inlet and a liquid outlet and equipped with at least one filter.

DETAILED DESCRIPTION OF THE INVENTION

Hereinafter, the present invention is described in detail.
The peptide having affinities for an immunoglobulin and/or an immune complex of the present invention is represented by the following amino acid sequence B (SEQ ID NO:1 of the sequence listing).

```
                    Thr Thr Tyr Lys Leu Val
    Ile Asn Gly Lys Thr Leu Lys Gly Glu Thr
    Thr Thr Lys Ala Val Asp Ala Glu Thr Ala
    Glu Arg Ala Phe Arg X01 Tyr Ala X02 Asp
    Asn Gly Val X03 Gly X04 Trp Thr Tyr Asp
    Pro Ala Thr Lys Thr Phe Thr Val Thr Glu
    Cys
```

(wherein, X01 is one species selected from three amino acids Asn, Lys and Gln, X02 is one species selected from two amino acids Thr and Asn, X03 is one species selected from two amino acids Glu and Asp, and X04 is one species selected from four amino acids Leu, Val, Ile and Met.)

In this description, the term "affinity" refers to a property to have binding activity for a certain compound. That is, the peptide having affinities for an immunoglobulin and/or an immune complex of the present invention is characterized in having binding activity for an immunoglobulin and/or an immune complex.

The peptide of the present invention was obtained from the investigations described below.

Firstly, the DNA shown under the SEQ ID NO:7 of the sequence listing (base sequence A) was prepared, which codes for a peptide (described in Japanese Patent No. 02764021 as a comparative peptide) (an amino acid sequence A: SEQ ID NO:6 of the sequence listing);

```
                    Thr Thr Tyr Lys Leu Val
    Ile Asn Gly Lys Thr Leu Lys Gly Glu Thr
    Thr Thr Lys Ala Val Asp Ala Glu Thr Ala
    Glu Lys Ala Phe Lys Gln Tyr Ala Asn Asp
    Asn Gly Val Asp Gly Val Trp Thr Tyr Asp
    Asp Ala Thr Lys Thr Phe Thr Val Thr Glu
``` and has a restriction enzyme site for inserting the above DNA into a vector. The restriction enzyme sites (NdeI, HindIII) of the above base sequence are intended for the vector used in Examples to be described hereinafter (pUCNT: WO 94/03613), but since it is well known in the art that different restriction sites are required for a different kind of vector, a detailed explanation on the subject is omitted. Thus, the DNA represented by the base sequence A was inserted into the vector pUCNT, *Escherichia coli* (HB101) was transformed with the vector having said DNA, the transformant cells were then cultured and homogenized, and the supernatant was purified to obtain a peptide. This peptide was immobilized on a carrier to give an immunoglobulin and/or immune complex adsorbent but its immunoglobulin and/or immune complex adsorption capacity was drastically decreased on irradiation with γ rays (25 kGy).

Then, based on said base sequence A, a DNA library of partially changed base sequences was prepared and explored in detail to see which amino acid residues should be substituted with what kinds of amino acids to increase the immunoglobulin- and/or immune complex-binding affinity and enhance the stability against radiation sterilization with γ-rays.

The exploration led to the finding that the optimum peptide is the one containing the following amino acid sequence B (SEQ ID NO:1 of the sequence listing) as produced by the producer strain obtained by the procedure comprising adding (cat atg) and (taa gct t) to the 5'-end and 3'-end, respectively, of the DNA represented by the following base sequence B (SEQ ID NO:2 of the sequence listing), inserting the construct into a vector, and transforming *E. coli* HB101 therewith. (Base sequence B: SEQ ID NO:2 of the sequence listing)

```
(Base sequence B: SEQ ID NO:2 of the
sequence listing)
                acc acc tat aaa ctg gtt
atc aac ggt aaa acc ctg aaa ggt gaa acc
acc acc aag gct gtt gac gct gaa acc gct
gag cgc gca ttt cgg X01 tat gct X02 gac
aac ggt gtc X03 ggt X04 tgg acc tat gac
ccc gct acc aaa acc ttt acc gtt acc gaa
tgc
wherein,
X01:    aac, aat, aaa, aag, caa, or cag
X02:    aca, acg, acc, act, aac, or aat
```

-continued

```
X03:      gaa, gag, gac, or gat

X04:      cta, ctg, ctc, ctt, tta, ttg, gta, gtg, gtc, gtt, ata, atc, att, or atg.
```

(Amino acid sequence B: SEQ ID NO:1 of
the sequence listing)

```
                                              Thr

Thr Tyr Lys Leu Val Ile Asn Gly Lys Thr

Leu Lys Gly Glu Thr Thr Thr Lys Ala Val

Asp Ala Glu Thr Ala Glu Arg Ala Phe Arg

X01 Tyr Ala X02 Asp Asn Gly Val X03 Gly

X04 Trp Thr Tyr Asp Pro Ala Thr Lys Thr

Phe Thr Val Thr Glu Cys
``` wherein,

```
X01:      Asn, Lys, or Gln

X02:      Thr or Asn

X03:      Glu or Asp

X04:      Leu, Val, Ile, or Met.
```

The peptide represented by the amino acid sequence B was immobilized on a carrier to construct an immunoglobulin and/or immune complex adsorbent. It was found that even when this adsorbent was subjected to irradiation with γ rays (25 kGy), the immunoglobulin and/or immune complex adsorption capacity of the adsorbent was equivalent to that of an unirradiated adsorbent.

By way of illustration, the peptide containing the amino acid sequence B, said peptide being shown under the SEQ ID NO:8 of the sequence listing (C36 peptide);

```
                                          Met Thr

Thr Tyr Lys Leu Val Ile Asn Gly Lys Thr

Leu Lys Gly Glu Thr Thr Thr Lys Ala Val

Asp Ala Glu Thr Ala Glu Arg Ala Phe Arg

Gln Tyr Ala Thr Asp Asn Gly Val Glu Gly

Met Trp Thr Tyr Asp Pro Ala Thr Lys Thr

Phe Thr Val Thr Glu Cys
``` was dissolved in physiological saline at a final concentration of 500 μg/mL and adjusted to pH 7.0 with an aqueous solution of sodium hydroxide and the resulting aqueous peptide solution was heated at 80° C. for 30 minutes and compared with the unheated aqueous peptide solution in IgG-binding capacity. No significant difference was found between them. The IgG-binding capacity was measured by passing each aqueous peptide solution through an immobilized IgG column (IgG Sepharose Fast Flow; product of Pharmacia), eluting the peptide in the indicated manner, and analyzing the eluate quantitatively by HPLC.

As such sequences containing the amino acid sequence shown under the SEQ ID NO:1, the sequences shown under the SEQ ID NO:10, 11, 13 and 15, for instance, can be mentioned.

Now, the nucleotide sequence, recombinant DNA and microorganism according to the present invention are described below.

The nucleotide sequence of the invention is characterized by its coding for at least one species of the amino acid sequence shown under the SEQ ID NO:1.

This nucleotide sequence preferably comprises at least one species of the base sequence shown under the SEQ ID NO:2. The sequence containing at least one species of the base sequence shown under the SEQ ID NO:2 includes the sequence shown under the SEQ ID NO:9, 12, 14 or 16, for example.

The recombinant DNA of the present invention is characterized by its having one or more nucleotide sequences coding for the amino acid sequence shown under the SEQ ID NO:1.

Referring to the above recombinant DNA, the nucleotide sequence preferably comprises at least one species of the base sequence shown under the SEQ ID NO:2.

The recombinant DNA of the invention can be constructed by the known chemical and genetic-engineering techniques described in, for example, Molecular Cloning 2nd Edt., Cold Spring Harbor Laboratory Press (1989), etc.

A DNA used in the construction of said recombinant DNA can be obtained, for example, by preparing a DNA library, in which the sequence thereof was partially modified base sequence A, and selecting the objective DNA by immunoscreening using said DNA library and an immunoglobulin and/or an immune complex.

Although the kind of said recombinant DNA is not restricted, it is preferably a plasmid or phage in view of the ease of gene manipulation. In constructing a plasmid, the pUCNT vector (WO 94/03613) or a commercial E. coli-derived vector, for instance, can be employed.

The microorganism of the present invention is characterized by its comprising at least one recombinant DNA having one or more nucleotide sequences coding for the amino acid sequence shown under the SEQ ID NO:1.

Referring to the above microorganism, the nucleotide sequence preferably comprises at least one species of the base sequence shown under the SEQ ID NO:2.

The microorganism of the invention can be prepared by transforming a microorganism with the above recombinant DNA in accordance with the known genetic engineering technology described in, for example, Basic Methods in Molecular Biology, Appleton & Lange (1986), for example by calcium phosphate transfection.

The microorganism which can be used for the preparation of the objective microorganism (transformant) includes *Escherichia coli* strains such as *E. coli* HB101 or the like microorganisms.

The adsorbent of the present invention is now described. The adsorbent for an immunoglobulin and/or an immune complex of the invention is characterized by its comprising a water-insoluble carrier having, as immobilized thereon, a peptide containing at least one species of the amino acid sequence shown under the SEQ ID NO:1 and consisting of not more than 70 amino acid residues.

The peptide which can be used for said adsorbent is not particularly restricted insofar as it contains at least one species of the amino acid sequence shown under the SEQ ID NO:1 and consisting of not more than 70 amino acid residues. Since the above peptide contains the amino acid sequence shown under the SEQ ID NO:1, it is characterized by its having affinities for an immunoglobulin and/or an immune complex.

Moreover, the above peptide is preferably a thermally stable peptide from the viewpoint that the peptide is able to withstand sterilization procedures. The thermally stable peptide mentioned above is a peptide such that its inherent properties will not be impaired even if heated to 80° C. or higher temperatures for 30 minutes whether in a lyophilized solid state or in an aqueous solution state, or its characteristics before sterilization will not be lost even if the peptide is immobilized on a carrier and subjected to autoclaving (115° C., 30 min.; 121° C., 20 min.; or 126° C., 15 min.) or radiation sterilization (25 kGy).

The water-insoluble carrier which can be used for the adsorbent of the invention includes inorganic carriers such as glass beads, silica gels, etc.; organic carriers composed of synthetic polymers, such as crosslinked polyvinyl alcohols, crosslinked polyacrylates, crosslinked polyacrylamides, crosslinked polystyrenes, etc., and/or polysaccharides such as crystalline cellulose, crosslinked cellulose, crosslinked agarose, crosslinked dextran, etc.; and various composite carriers each comprising an organic-organic composite, an organic-inorganic composite or the like composite, etc. Among these, hydrophilic carriers are preferred in view of their high adsorption selectivity for an immunoglobulin and/or an immune complex with a comparative freedom from nonspecific adsorption.

The term "hydrophilic carrier" as used in this specification means a carrier such that, when the compound composing the carrier is molded into a flat sheet, its contact angle with respect to water is not more than 60 degrees. As representative examples of such carrier, there can be mentioned carriers made of polysaccharides such as cellulose, chitosan, dextran, etc., polyvinyl alcohol, a saponified ethylene-vinyl acetate copolymer, polyacrylamides, polyacrylic acid, polymethacrylic acid, poly (methyl methacrylate), polyacrylic acid-grafted polyethylene, polyacrylamide-grafted polyethylene, and glass.

As commercial products, there can be mentioned GCL2000 and GC700 which are porous cellulose gels, Sephacryl S-1000 which is a covalently crosslinked allyl-dextran-methylenebisacrylamide, TOYOPEARL which is an acrylate carrier, Sepharose CL4B which is an agarose type crosslinked carrier, and Eupergit C250L which is an epoxy-activated polymethacrylamide, to mention but a few examples. It goes without saying, however, that the carrier for the invention is not limited to these carriers and activated carriers. The carriers mentioned above may be used each independently or as a suitable mixture of two or more species.

The water-insoluble carrier for use in the present invention is preferably one having a large surface area in view of the intended use according to the invention, namely adsorption of an immunoglobulin and/or an immune complex, and the technological feature of the invention which utilizes the affinity of the peptide for these, that is to say a porous carrier having a multiplicity of appropriately-sized pores. As specific examples of such a porous carrier, the above-mentioned hydrophilic carriers available from commercial sources may be mentioned.

The exclusion limit of molecular weight of the porous carrier according to the invention is not less than 150,000 but the molecular weight of immunoglobulin class G (IgG) ranges from 140,000 to 170,000 and, therefore, in order that the IgG may be efficiently adsorbed with a porous carrier, the exclusion limit of molecular weight of the carrier is preferably not less than 250,000 which is larger than the molecular weight of IgG. Moreover, it is difficult to predict the molecular weight of the immune complex involving said immunoglobulin as a constituent but assuming that the immunoglobulin G4 molecule forms an immune complex with an antigen, the molecular weight of the complex is calculated to be not less than 560,000. Therefore, in order that the immunoglobulin and/or immune complex may be admitted into a porous carrier, the exclusion limit of molecular weight of the carrier is preferably not less than 600,000 and in order that it may be done so easily, the exclusion limit of molecular weight is more preferably not less than 3,000,000.

With regard to the porous structure of said water-insoluble carrier, considering the adsorption capacity per unit volume of the adsorbent, total porosity (a structure such that the carrier is porous in its entirety to permit ingress of the molecules to be adsorbed into the interior zone) is preferred to surface porosity (a structure such that the carrier is porous in the exterior zone but dense in the interior zone). More preferably, the carrier has a void volume of not less than 20% as measured by mercury porosimetry and a specific surface area of not less than 1 $m^2/g$ as measured by mercury porosimetry.

Referring to the morphology of the water-insoluble carrier, it may assume various forms such as beads, filaments, membranes (inclusive of hollow fiber), and so forth and any of these forms can be liberally chosen. Beads are particularly preferred in view of the ease of constructing a carrier having a defined exclusion limit of molecular weight. Beads having an average particle diameter of 10 to 2,500 μm are easy to use and particularly those within the size range of 25 μm to 800 μm are recommended from the standpoint of the ease with which the ligand coupling reaction may take place.

Furthermore, the presence of a functional group useful for said ligand coupling reaction on the surface of said water-insoluble carrier is advantageous for the purpose of coupling the ligand. Among representative examples of said functional group are hydroxyl, amino, aldehyde, carboxyl, thiol, silanol, amido, epoxy, succinylimido, acid anhydride groups, etc.

The water-insoluble carrier which can be used in the invention may be whichever of a hard carrier and a soft carrier but it is an important factor in its use as an adsorbent for extracorporeal circulation treatment that when it is packed into a column and a fluid is run thereon, no plugging troubles will take place. For this purpose, a sufficient mechanical strength is required. Therefore, the water-insoluble carrier for use in the invention is more preferably a hard carrier.

As used in this specification, the term "hard carrier" means a carrier such that, taking a granular gel as an example, when the gel is evenly packed into a glass cylinder (inside diameter; 9 mm: column length; 150 mm) under the following conditions and a hydrous fluid is passed through the column, the relation between pressure loss ΔP and flow rate is linear up to 0.3 $kg/cm^2$.

By way of illustration, glass cylindric column (inside diameter; 9 mm: column length; 150 mm) each equipped with a filter having a pore size of 15 μm at either end were uniformly packed with agarose gel (Biogel-A5m, product of Bio-Rad, particle size 50 to 100 mesh), a vinyl polymer gel (TOYOPEARL HW-65, product of TOSOH, particle size 50 to 100 μm), and a cellulose gel (Cellulofine GC-700m, product of Chisso Corporation, particle size 45 to 105 μm), respectively, and using a peristaltic pump, water was passed through each column to determine the relationship of flow rate to pressure loss ΔP (FIG. 1). The flow rate (cm/min.) was plotted on the ordinate and the pressure loss (kg/cm²) was plotted on the abscissa. In the figure, o represents TOYOPEARL HW-65, Δ Cellulofine GC-700m, and ● Biogel-A5m. It was found that whereas the flow rate was increased in approximate proportion to the pressure gain in the cases of TOYOPEARL HW-65 and Cellulofine GC-700m, compaction occurred in the case of Biogel-A5m so that increasing the pressure did not increase the flow rate.

The method of immobilizing said peptide on a water-insoluble carrier is now described.

In immobilizing a peptide having affinities for an immunoglobulin and/or an immune complex, namely a peptide containing at least one species of the amino acid sequence shown under the SEQ ID NO:1 and consisting of not more than 70 amino acid residues on the water-insoluble carrier described hereinabove, it is more preferable to improve the adsorption efficiency through reducing the steric hindrance of the peptide and, for suppression of non-specific adsorption, immobilize the peptide through a hydrophilic spacer. As the hydrophilic spacer, a poly(alkylene oxide) derivative as substituted with a carboxyl, amino, aldehyde, epoxy or the like group at either terminus, etc. is preferably used.

The method of immobilizing said peptide having affinities for an immunoglobulin and/or an immune complex or said hydrophilic spacer is not particularly restricted. Thus, the technology used in immobilizing a protein or peptide on a carrier, in general, can be employed. This technology includes (1) the method which comprises reacting the carrier with cyanogen bromide, epichlorohydrin, diglycidyl ether, tosyl chloride, tresyl chloride, hydrazine or the like to activate the carrier (converting the functional group originally present on the carrier to a functional group with which the compound to be immobilized as a ligand may react more readily) and reacting it with the ligand compound and (2) the method which comprises adding a condensing agent, such as carbodiimide, or a reagent having a plurality of functional groups per molecule, such as glutaraldehyde, to a system comprising both the carrier and the compound to be immobilized as a ligand to thereby effect condensation or crosslinking. In order to provide an adsorbent useful for extracorporeal circulation treatment and hemocatharsis, it is more preferable to adopt an immobilization protocol which does not easily allow release of the protein or the like from the carrier during sterilization or treatment.

The adsorption method of the present invention is characterized by its comprising bringing said adsorbent into contact with a body fluid containing an immunoglobulin and/or an immune complex.

A variety of methods are available for bringing an adsorbent comprising a carrier and a peptide having affinities for an immunoglobulin and/or an immune complex as immobilized thereon into contact with a body fluid such as blood, plasma or serum to adsorb an immunoglobulin and/or an immune complex in the body fluid. Among representative methods are (1) the method which comprises withdrawing a body fluid and pooling it in a bag or the like, mixing it with the adsorbent to adsorb an immunoglobulin and/or an immune complex thereon, and filtering off the adsorbent to recover the body fluid deprived of an immunoglobulin and/or an immune complex and (2) the method which comprises filling the adsorbent into a container having a body fluid inlet and a body fluid outlet and equipped with a filter which is permeable to the body fluid but impermeable to the adsorbent at said outlet and passing the body fluid through the container. Although whichever of the methods can be used, the adsorbent of the invention is suited to the latter method which is simple procedure-wise, and by applying it to an extracorporeal circuit, an immunoglobulin and/or an immune complex can be removed from the patient's body fluid efficiently on line.

Adsorption unit of the present invention comprises the adsorbent of the present invention filled in a container having a liquid inlet and a liquid outlet and equipped with at least one filter.

Next, the adsorption unit for an immunoglobulin and/or an immune complex of the present invention using the above adsorbent adsorbing an immunoglobulin and/or an immune complex is explained on the basis of its schematic sectional view.

Adsorption unit 7 shown in FIG. 2 comprises a liquid inlet 1, a liquid outlet 2, an adsorbent 3 of the present invention for an immunoglobulin and/or an immune complex, filters 4 and 5 through which liquid and components contained in the liquid can pass but the adsorbent for an immunoglobulin and/or an immune complex cannot pass, and a column 6.

The shape and material of this container are not particularly restricted, but preferably, for example, a tube container having a content of about 20 to 400 mL and a diameter of about 2 to 10 cm may be used.

The above filter is not particularly restricted as long as liquid and components contained in the liquid can pass through but the adsorbent for an immunoglobulin and/or an immune complex cannot pass through it.

EXPLANATION OF NUMERALS

Figure 1:
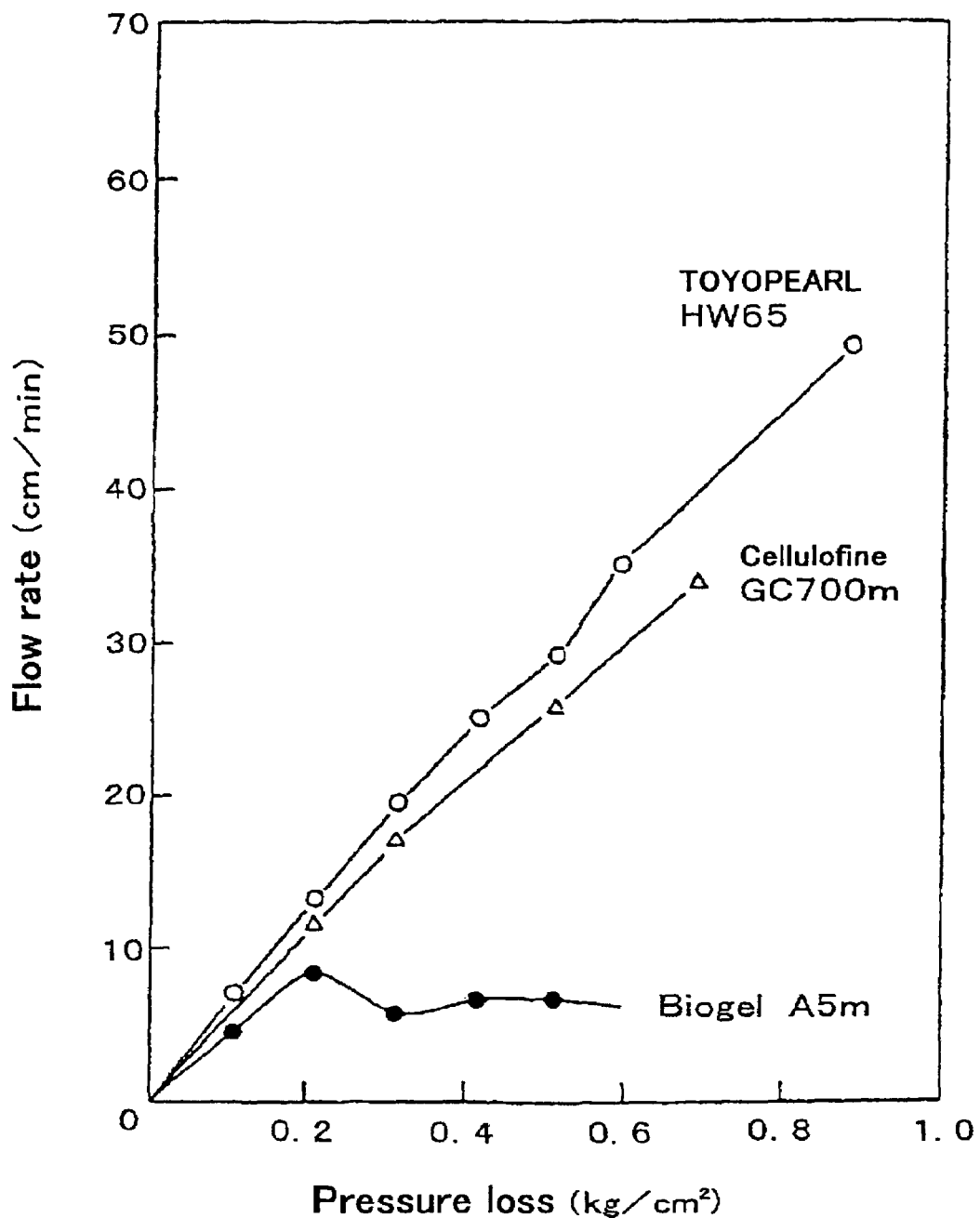
FIG. 1 is a graph showing the result of researching a flow rate and a pressure loss using three species of gels, i.e. TOYOPEARL HW-65, Cellulofine GC-700m and Biogel-A5m.
Figure 2:
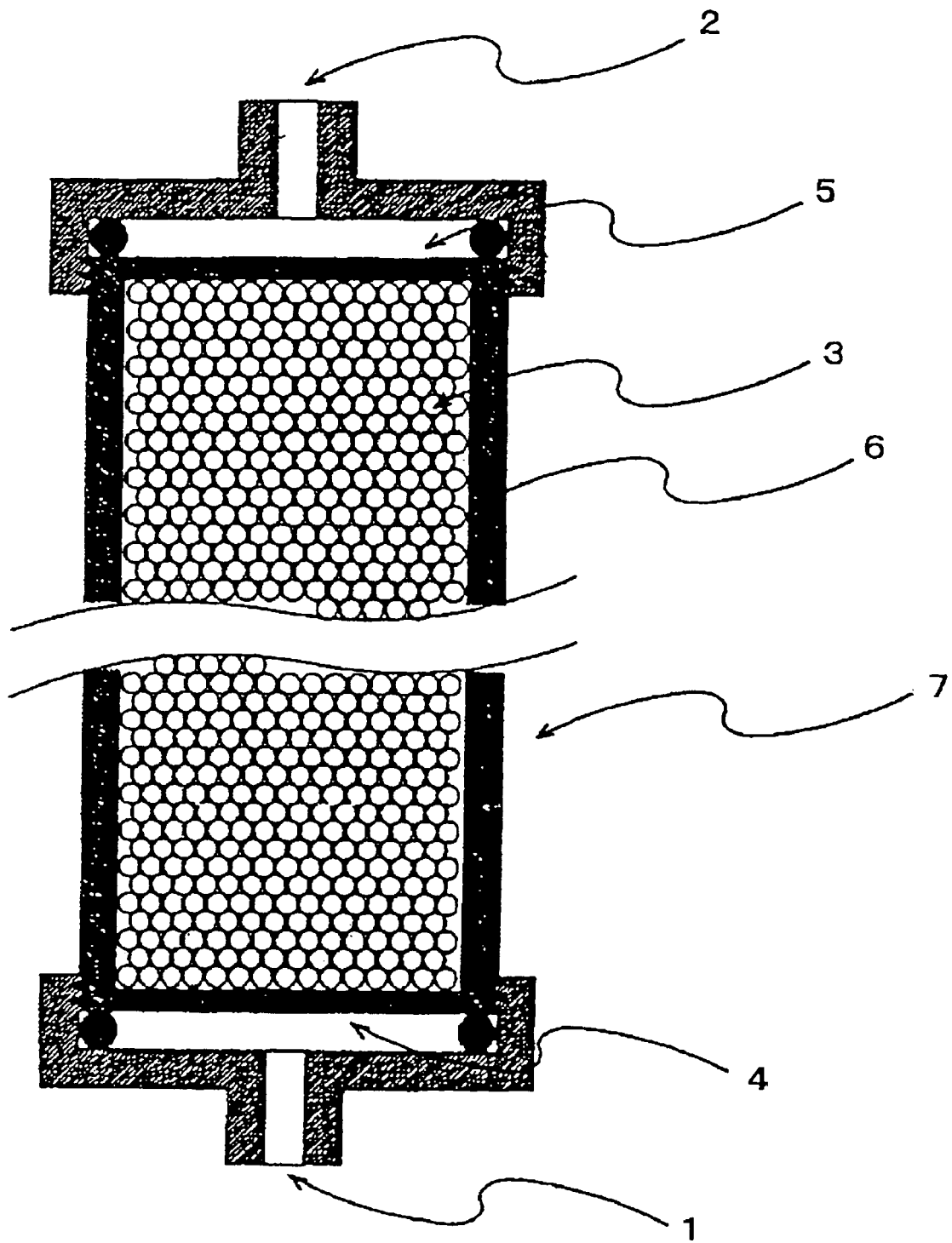
FIG. 2 is a schematic sectional view showing one example of the adsorption unit for an immunoglobulin and/or an immune complex of the present invention.

1: Liquid inlet
2: Liquid outlet
3: Adsorbent
4: Filter
5: Filter
6: Column
7: Adsorption unit

BEST MODE FOR CARRYING OUT THE INVENTION

In the following, the present invention is described in further detail by way of Examples. However, the present invention is not limited to the following Examples. Additionally, in this description, various amino acid residues are indicated as the following abbreviations. Ala; an L-alanine residue, Arg; an L-arginine residue, Asp; an L-aspartic acid residue, Asn; an L-asparagine residue, Cys; an L-cysteine residue, Gln; an L-glutamine residue, Glu; an L-glutamic acid residue, Gly; an L-glycine residue, His; an L-histidine residue, Ile; an L-isoleucine residue, Leu; an L-leucine residue, Lys; an L-lysine residue, Met; an L-methionine residue, Phe; an L-phenylalanine residue, Pro; an L-proline residue, Ser; an L-serine residue, Thr; an L-threonine residue, Trp; an L-tryptophan residue, Tyr; an L-tyrosine residue, and Val; an L-valine residue. Additionally, in this description, the amino acid sequence of a peptide is described according to a usual manner so that the amino terminus (hereinafter referred to as N-terminus) is located in the left side and a carboxyl terminus (hereinafter referred to as C-terminus) is located in the right side.

EXAMPLE 1

Immobilization of IgG-binding Protein (C36) on a Porous Carrier (Kac)

<Production of C36 Peptide>

Based on the DNA coding for the C36 peptide shown under the SEQ ID NO:8 of the sequence listing, a DNA shown under the SEQ ID NO:9 of the sequence listing was designed and synthesized so that it could be ligated to pUCNT vector (WO 94/03613) by using the restriction enzyme sites of NdeI and Hind III for the 5'-end and 3'-end, respectively.

The DNA containing the sequence shown under the SEQ ID NO:9 was ligated to the pUCNT vector cleaved open by digestion with the restriction enzymes NdeI and HindIII (products of Takara Shuzo) using DNA Ligation Kit Ver. 2 (product of Takara Shuzo) in accordance with the manual to construct a pUCNT-C36 vector. Using DNA Ligation Kit Ver. 1 (product of Takara Shuzo) according to the manual, the above pUCNT-C36 vector was introduced into *Escherichia coli* HB101 (marketed by Funakoshi) and a transformant screening was carried out using resistance to the antibiotic ampicillin as an indicator. Moreover, from the transformant, the plasmid DNA was extracted and sequenced using Flexi Prep (trade mark) (product of Amersham Pharmacia Biotech) in accordance with the manual to verify that the pUCNT-C36 vector had the designed DNA sequence.

Then, this transformant was shake-cultured in 6 L of L-broth (5 g/L NaCl, 10 g/L bactotrypsin, 5 g/L yeast extract) at 37° C. for 20 hours and the cultured cells were centrifugally recovered (using Hitachi RPR9-2 rotor, 4° C., 6,000 rpm, 20 min.) The pellet obtained was suspended in 300 mL of TE buffer (20 mM Tris-HCl, 1 mM EDTA, pH 7.5) and sonicated (using BRANSON 250, on ice, 6 min.×3) and the supernatant was centrifugally recovered (using Hitachi RPR16 rotor, 4° C., 15,000 rpm, 20 min.). This supernatant was heat-treated at 70° C. for 10 minutes and further centrifuged (using Hitachi RPR16 rotor, 4° C., 15,000 rpm, 20 min.) and the supernatant, 300 mL, was recovered. Using a high performance liquid chromatograph (column: μBondasphere C18, product of Waters Japan), 40 mL of acetonitrile solution was passed at a flow rate of 5 mL/min to activate the column in advance and a 300 mL sample was run onto the column at the same flow rate. The column was washed with 200 mL of 0.1% TFA+64% acetonitrile solution and the objective C36 peptide was eluted with 200 mL of 0.1% TFA (trifluoroacetic acid)+40% acetonitrile solution. The eluate was concentrated to 100 mL on an evaporator and lyophilized to give a high-purity sample.

<Epoxidation of a Cellulose Gel>

Water was added to 90 mL of our trial product Kac gel, which is a cellulosic porous hard gel and has an exclusion limit of molecular weight for spherical protein of 5,000,000 or more, in an amount for the total amount became 180 mL. Then, 60 mL of 2 N sodium hydroxide was added, and the mixture was adjusted to 40° C. 21 mL of epichlorohydrin was added thereto and the mixture was subjected to reaction under stirring at 40° C. for 2 hours. After completion of the reaction, the resultant was sufficiently washed with water to obtain an epoxy-activated Kac gel.

<Immobilization of C36 Peptide>

C36peptide (10 mg) was dissolved in 0.5 mL of 0.05 M boric acid buffer (pH 10). Then, the mixture was readjusted to pH 10 by adding 0.01 N sodium hydroxide solution in an amount for the total amount became 1.0 mL (C36 peptide solution). After adding the peptide solution (whole quantity) to 1 mL of the above epoxy-activated Kac gel, the mixture was shaken at 37° C. for 16 hours and washed with sufficient amount of PBS (10 mM phosphate buffer containing 150 mM sodium chloride) to obtain Kac-C36.

EXAMPLE 2

Immobilization of IgG-binding Protein (B04) on a Porous Carrier (Sephacryl S1000)

<Production of the B04 Peptide>

Using Peptide Synthesizer Model 4170 (product of Pharmacia LKB), the peptide shown under the SEQ ID NO:10 of the sequence listing was synthesized as below by the solid-phase synthesis method. Using 0.1 mmol of Fmoc-glutamine NovaSyn KA (product of Pharmacia LKB), a C-terminal glutamine-coupled carrier, the deprotection reaction and condensation reaction were sequentially repeated toward the N-terminus for peptide chain extension in accordance with the synthesizing program loaded in said peptide synthesizer. Thus, the 9-fluorenylmethyloxycarbonyl (briefly, Fmoc) group protecting the α-amino group of each amino acid was removed with piperidine and, after washing with N,N-dimethylformamide (briefly, DMF), the condensation reaction was carried out using 2-(1H-benzotriazol-1-yl)-1,1,3,3-tetramethyluronium tetrafluoroborate and N,N-diisopropylethylamine, followed by washing with DMF. The above procedure was repeated. The amino acid was used in the form of Fmoc-L-Ala, Fmoc-L-Asn (Trt), Fmoc-L-Asp (OtBu), Fmoc-L-Cys (Trt), Fmoc-L-Gln (Trt), Fmoc-L-Glu (OtBu), Fmoc-L-Gly, Fmoc-L-Ile, Fmoc-L-Leu, Fmoc-L-Lys (Boc), Fmoc-L-Phe, Fmoc-L-Thr (tBu), Fmoc-L-Trp, Fmoc-L-Tyr (tBu) or Fmoc-L-Val with the amount of about 5-fold in mol (0.5 mmol) to substrates in a vial (wherein Trt, tBu, Boc, and OtBu represent a trityl group, a tertiary butyl ester, a tertiary butyl oxycarbonyl group, and an O-tertiary butyl group, respectively).

<Deprotection Reaction and Excision of the Peptide Chain>

Upon completion of the reaction procedure for all the amino acids, the resulting carrier was serially washed on a 3G-3 (pore) glass filter using tert-amyl alcohol, acetic acid, and diethyl ether in the order mentioned and then dried in vacuo to give a dry carrier. To 1 g of the above carrier in a vial, 20 mL of trifluoroacetic acid (briefly, TFA), 260 μL of 1,2-ethanedithiol, and 780 μL of anisole were added and the mixture was stirred at room temperature for 1.5 hours. Then, this mixture was filtered through a 3G-3 (pore) glass filter to separate the carrier and the filtrate was concentrated under reduced pressure at 35° C. To the residue was added pre-cooled anhydrous diethyl ether until precipitates had ceased to appear, followed by stirring. The mixture was then centrifuged and the crude peptide pellet was recovered. This crude peptide was washed with several portions of anhydrous diethyl ether and dried under reduced pressure to give the objective semi-purified peptide.

<Purification of the Peptide>

The above semi-purified peptide was dissolved in 0.1% TFA and subjected to high-speed centrifugation at 3,000 rpm. The supernatant was filtered through a 0.45 μm membrane filter and the filtrate was subjected to high performance liquid chromatography (HPLC). As the HPLC, Model LC-10A system (manufactured by Shimadzu Corporation) was used and the column used was the reversed-phase µBondasphere C18 (Waters Japan). As the mobile phase, 0.1% aqueous solution of TFA was used for solution A and 0.1% TFA-containing 80% (v/v) acetonitrile/$H_2O$ for solution B, and elution was carried out on a linear concentration gradient from A to B. The fractions corresponding to the chromatographic peak were pooled and recovered. This fractional recovery procedure was repeated a few times and the product was lyophilized to give a pure peptide. This peptide was analyzed for its amino acid sequence using Gas-phase Protein Sequencer 477A (manufactured by Applied Biosystems) and Hitachi Custom Ion Exchange Resin to verify that the peptide obtained above has the amino acid sequence shown under the SEQ ID NO:10 of the sequence listing described below.

<Epoxy Activation of Sephacryl S1000>

Water was added to 90 mL of Sephacryl S1000 (product of Amersham Pharmacia Biotech: exclusion limit of molecular weight for spherical protein; ca 8,000,000), a porous hard gel with a pore diameter of 400 nm, in an amount for the total amount became 180 mL, 60 mL of 2 N-sodium hydroxide was added thereto, and the temperature was adjusted to 40° C. To this solution was added 21 mL of epichlorohydrin, and the reaction was carried out under stirring at 40° C. for 2 hours. After completion of the reaction, the product was sufficiently washed with water to give an epoxy-activated Sephacryl S1000.

<Immobilization of B04 Peptide>

Using 30 mg of B04 peptide in lieu of 10 mg of C36 peptide and the epoxy-activated Sephacryl S1000 gel in lieu of the epoxy-activated Kac gel, the corresponding procedure of Example 1 was otherwise repeated to give Sephacryl S1000-B04 on which B04 peptide was immobilized.

EXAMPLE 3

Immobilization of IgG-binding Protein ($CO_4$) on a Porous Carrier (GCL2000m)

<Production of CO4 Peptide>

The DNA coding for the CO4 peptide shown under the SEQ ID NO:11 of the sequence listing was designed as the one shown under the SEQ ID NO:12 of the sequence listing, synthesized, and made ligatable to pUCNT vector in the same manner as in Example 1.

Using the same protocol as in Example 1, the DNA having the sequence of the SEQ ID NO:12 was introduced into pUCNT vector to construct pUCNT-$CO_4$ vector.

Furthermore, also as in Example 1, an *E. coli* transformant was constructed, cultured in 6 L of L-broth, and purified to give the objective high-purity $CO_4$ peptide for use in various studies.

<Epoxidation of GCL2000 m>

Water was added to 90 mL of the cellulosic porous hard gel GCL2000m (product of Chisso Corporation: exclusion limit of molecular weight for spherical protein; 3,000,000) in an amount for the total amount became 180 mL. Then, 60 mL of 2 N-sodium hydroxide was added and the mixture was adjusted to 40° C. To this solution was added 21 mL of epichlorohydrin, and the reaction was carried out under stirring at 40° C. for 2 hours. After completion of the reaction, the product was sufficiently washed with water to give an epoxy-activated GCL2000m.

<Immobilization of C04 Peptide>

Using C04 peptide in lieu of C36 peptide and the epoxy-activated GCL2000m gel in lieu of the epoxy-activated Kac gel, the corresponding procedure of Example 1 was otherwise repeated to give GCL2000m-C04 on which C4 peptide was immobilized.

EXAMPLE 4

Immobilization of IgG-binding Protein (C15) on a Porous Carrier (CNBr-Activated Sepharose 4B)

<Production of C15 Peptide>

The DNA coding for the C15 peptide of the SEQ ID NO:13 of the sequence listing was designed as the one shown under the SEQ ID NO:14 of the sequence listing, synthesized, and made ligatable to pUCNT vector in the same manner as in Example 1.

Using the same protocol as in Example 1, the DNA having the sequence of the SEQ ID NO:14 was introduced into pUCNT vector to construct pUCNT-C15 vector.

Furthermore, also as in Example 1, an *E. coli* transformant was constructed, cultured in 6 L of L-broth, and purified to give the objective high-purity C15 peptide for use in various studies.

<Immobilization of C15 Peptide>

CNBr-activated Sepharose 4B (product of Amersham Pharmacia Biotech: exclusion limit of molecular weight for spherical protein; ca 20,000,000) (1 g) was caused to swell with a small amount of 1 mM aqueous hydrochloric acid solution for 15 minutes, washed with 1 mM aqueous hydrochloric acid solution, and further washed with coupling buffer (0.5 M sodium chloride, 0.1 M sodium hydrogencarbonate, pH 8.3). In 1 mL of coupling buffer was dissolved 10 mg of C15 peptide, and the above washed gel was added and reacted at 4° C. for 16 hours. After the reaction product was washed with coupling buffer, block buffer (0.2 M glycine, 0.5 M sodium chloride, 0.1 M sodium hydrogencarbonate, pH 8.3) was added and the reaction was carried out at room temperature for 2 hours. The reaction mixture was washed with 2 kinds of after-treatment buffers, i.e. (0.5M sodium chloride, 0.1M acetic acid-sodium acetate buffer, pH 4.0) and (0.5 M sodium chloride, 0.1 M Tris-HCl buffer, pH 8.0), alternatingly 3 times each to give a Sepharose 4B-C15.

EXAMPLE 5

Immobilization of IgG-binding Protein (C24) on a Porous Carrier (Tresyl TOYOPEARL (Product of TOSOH: Exclusion Limit of Molecular Weight for Spherical Protein; ca 5,000,000))

<Production of C24 Peptide>

The DNA coding for the C24 peptide of the SEQ ID NO:15 of the sequence listing was designed as the one shown under the SEQ ID NO:16, synthesized, and made ligatable to pUCNT vector in the same manner as in Example 1.

Using the same protocol as in Example 1, the DNA having the sequence of the SEQ ID NO:16 was introduced into pUCNT vector to construct pUCNT-C24 vector.

Furthermore, also as in Example 1, an *E. coli* transformant was constructed, cultured in 6 L of L-broth, and purified to give the objective high-purity C24 peptide for use in various studies.

<Immobilization of C24 Peptide>

In 1 mL of coupling buffer (0.5 M sodium chloride, 0.1 M carbonate buffer, pH 8.3) was dissolved 5 mg of C24 peptide, followed by addition of 200 mg (dry weight) of AF-tresyl-TOYOPEARL 650, and the reaction was carried out at 4° C. overnight. After the reaction product was washed with 0.5 M aqueous sodium chloride solution, block buffer (0.5 M sodium chloride, 0.1 M Tris-HCl buffer, pH 8.0) was added and the reaction was carried out at room temperature for 2 hours. Then, it was further washed with 0.5 M aqueous sodium chloride solution to give TOYOPEARL-C24.

EXAMPLE 6

Immobilization of IgG-binding Protein (C36) on a Porous Carrier (Sepharose 6B)

<Epoxidation of Sepharose 6B>

Water was added to 90 mL of Sepharose 6B (product of Amersham Pharmacia Biotech: exclusion limit of molecular weight for spherical protein; ca 4,000,000), which is an agarose beady gel, in an amount for the total amount became 180 mL. Then, 60 mL of 2 N sodium hydroxide was added, and the mixture was adjusted to 40° C. 21 mL of epichlorohydrin was added thereto and the mixture was subjected to reaction under stirring at 40° C. for 2 hours. After completion of the reaction, the resultant was washed sufficiently with water to obtain an epoxy-activated Sepharose 6B gel.

<Immobilization of C36 Peptide>

Using the epoxy-activated Sepharose 6B in lieu of the epoxy-activated Kac gel, the corresponding procedure of Example 1 was otherwise repeated to give Sepharose 6B-C36 on which C36 peptide was immobilized.

COMPARATIVE EXAMPLE 1

Immobilization of IgG-binding Protein (Protein G) on a Porous Carrier (GCL2000m)

<Immobilization of Protein G>

Using 4 mg of protein G (product of Sigma) in lieu of 10 mg of the C36 peptide and the epoxy-activated GCL2000m gel prepared in Example 3 in lieu of the epoxy-activated Kac gel, the corresponding procedure of Example 1 was otherwise repeated to give GCL2000m-protein G on which protein G was immobilized.

COMPARATIVE EXAMPLE 2

Immobilization of IgG-binding Protein (Protein A) on a Porous Carrier (Kac)

<Immobilization of Protein A>

Using 4 mg of protein A (product of Sigma) in lieu of 10 mg of the C36 peptide, the corresponding procedure of Example 1 was otherwise repeated to give Kac-protein A on which protein A was immobilized.

COMPARATIVE EXAMPLE 3

Immobilization of IgG-binding Peptide (MG56) on a Porous Carrier (Sepharose 6B)

<Production of MG56 Peptide>

The DNA coding for the peptide (SEQ ID NO:17 of the sequence listing) having the 57-residue sequence of protein G C3 domain with methionine added to its N-terminus was designed as the one shown under the SEQ ID NO:18, synthesized, and made ligatable to pUCNT vector in the same manner as in Example 1.

Using the same protocol as in Example 1, the DNA having the sequence of the SEQ ID NO:18 was introduced into pUCNT vector to construct pUCNT-MG56 vector.

Furthermore, also as in Example 1, an $E.\ coli$ transformant was constructed, cultured in 6 L of L-broth, and purified to give the objective high-purity MG56 peptide for use in various studies.

<Immobilization of the Peptide>

The above peptide was immobilized on a porous Sepharose to produce an adsorbent as described below. As the sepharose, thiopropyl-Sepharose 6B (product of Amersham Pharmacia Biotech) was used. To 50 mg of the thiopropyl-Sepharose 6B was added 50 mL of distilled water, and the mixture was allowed to stand at room temperature for 15 minutes to let the resin swell. The distilled water was then removed and replaced with 0.5 M NaCl-containing 0.1 M Tris-HCl (pH 7.5) coupling buffer.

On the other hand, 4 mg of the above purified peptide was dissolved in 400 µL of 0.5 M NaCl-containing 0.1 M Tris-HCl (pH 7.5) coupling buffer and the above swollen thiopropyl-Sepharose 6B (150 µL) was added. The mixture was stirred at 4° C. for 12 hours and, then, washed with sufficient PBS (150 µM sodium chloride-containing 10 mM phosphate buffer, pH 7.5) to give Sepharose 6B-MG56.

EXAMPLE 7

Evaluation of the IgG Adsorption Capacity of the Synthesized Adsorbent

The radiation sterilization of 0.5 mL each of the adsorbent GCL2000m-C04 synthesized in Example 3 and the adsorbent GCL2000m-protein G synthesized in Comparative Example 1 with cobalt 60 γ rays (25 KGy, 3 hrs.) was commissioned to Koga Isotope CO., LTD.

Each adsorbent, 100 µL, was taken in a vial, 300 µL of healthy human serum was added, and the mixture was shaken at 37° C. for 2 hours to effect adsorption. This suspension was centrifuged at 5,000 rpm for 1 minute and the determination of IgG concentration of the supernatant was commissioned to Shionogi Biomedical Laboratories.

As a control experiment, 100 µL of physiological saline instead of the adsorbent was taken in a vial, the same treatment as above was carried out, and the concentration of IgG in the solution was determined.

The adsorption ratio of IgG (%) was calculated by the following formulas. The results are shown in Table 1.

$$\text{Adsorption ratio (\%)} = \{(V1r - V1t/V1r)\} \times 100$$

V1r: The IgG concentration in a control experiment solution
V1t: The IgG concentration in an adsorption experiment supernatant

TABLE 1

|  | Adsorbent | Adsorption ratio of IgG before sterilization (%) | Adsorption ratio of IgG after sterilization (%) |
|---|---|---|---|
| Example 3 | GCL2000m-C04 | 97.1 | 90.2 |
| Comparative Example 1 | GCL2000m-Protein G | 98.6 | 59.8 |

EXAMPLE 8

Evaluation of the Anti-β1 Adrenoceptor Antibody Adsorption Capacities of Synthesized Adsorbents The radiation sterilization of 0.5 mL each of the adsorbent Kac-C36 synthesized in Example 1 and the adsorbent Kac-protein A synthesized in Comparative Example 2 with cobalt 60 γ rays (25 KGy, 3 hrs.) was commissioned to Koga Isotope CO., LTD.

Each adsorbent, 100 μL, was taken in a vial, 300 μL of the anti-β1 adrenoceptor antibody-positive serum of patients with dilated cardiomyopathy was added, and the mixture was shaken at 37° C. for 2 hours to effect adsorption. This suspension was centrifuged at 5,000 rpm for 1 minute and the anti-β1-adrenoceptor antibody titer of the supernatant was determined by ELISA.

The particulars of ELISA are as follows.

A 50 μg/mL (50 μL) solution of the second loop fragment peptide (SEQ ID NO:19) of the β1-adrenoceptor synthesized by Kurabo Industries, Ltd. on a commission basis was added to an ELISA plate and allowed to stand at 4° C. overnight. After plate washing, 100 μL of skim milk (product of Difco) solution was added, and the plate was allowed to sit at room temperature for 1 hour. After plate washing, 50 μL of the test sample (a 10-fold dilution of the above-mentioned supernatant) was added and the plate was allowed to sit at 4° C. overnight. The plate was washed again, 100 μL of a solution of biotinylated anti-human IgG antibody (product of Southern Biotechnology) was added, and the plate was allowed to sit at room temperature for 1 hour. After plate washing, 100 μL of substrate solution was added, and the plate was allowed to sit at room temperature for 30 minutes, after which the absorbance at 405 nm was measured. The β1 adrenoceptor adsorption capacity of each adsorbent was calculated from the absorbance (corresponding to 0% adsorption capacity) measured with the serum of patients with dilated cardiomyopathy in lieu of the above test sample and the absorbance (corresponding to 100% adsorption capacity) measured with healthy human serum. The results are shown in Table 2.

TABLE 2

| | Adsorbent | Adsorption ratio of β1 adrenoceptor (%) |
|---|---|---|
| Example 1 | Kac-C36 | 77.8 |
| Comparative Example 2 | Kac-Protein A | 52.5 |

EXAMPLE 9

Evaluation of the Rheumatoid Factor Adsorption Capacities of Synthesized Adsorbents The radiation sterilization of 0.5 mL each of the adsorbent Sepharose 6B-C36 synthesized in Example 6 and the adsorbent Sepharose 6B-MG56 synthesized in Comparative Example 3 with cobalt 60 γ rays (25 KGy, 3 hrs.) was commissioned to Koga Isotope CO., LTD.

Each adsorbent, 100 μL, was taken in a vial, 600 μL of the serum of rheumatism patients was added, and the mixture was shaken at 37° C. for 2 hours to effect adsorption. This suspension was centrifuged at 5,000 rpm for 1 minute and the determination of rheumatoid factor concentration in the supernatant was commissioned to Shionogi Biomedical Laboratories.

As a control experiment, 100 μL of physiological saline in lieu of the adsorbent was taken in a vial, the same treatment as above was carried out, and the rheumatoid factor concentration in the solution was similarly determined.

The adsorption ratio of a rheumatoid factor (%) was calculated by the following formulas. The results are shown in Table 3.

Adsorption ratio (%)={(V2r−V2t/V2r)}×100

V2r: The rheumatoid factor concentration in a control experiment solution

V2t: The rheumatoid factor concentration in an adsorption experiment supernatant

TABLE 3

| | Adsorbent | Adsorption ratio of rheumatoid factor (%) |
|---|---|---|
| Example 6 | Sepharose 6B-C36 | 56.3 |
| Comparative Example 3 | Sepharose 6B-MG56 | 34.4 |

EXAMPLE 10

Evaluation of the Immune Complex Adsorption Capacities of Synthesized Adsorbents The radiation sterilization of 0.5 mL each of the adsorbents synthesized in Examples 2, 4, and 5, i.e. Sephacryl S1000-B04, Sepharose 4B-C15, and TOYOPEARL-C24, respectively, with cobalt 60 γ rays (25 KGy, 3 hrs.) was commissioned to Koga Isotope CO., LTD.

The immune complex was prepared by heating a human IgG solution (10 mg/mL) at 63° C. for 15 minutes.

Each adsorbent, 100 μL, was taken in a vial, 300 μL of healthy human serum to which the above immune complex solution had been added at a concentration of 20 μg/mL was added, and the mixture was shaken at 37° C. for 2 hours to effect adsorption. This suspension was centrifuged at 5,000 rpm for 1 minute, and using Furelyzer C1q-CIC Kit, product of Fujirebio, Inc., the the immune complex concentration in the supernatant was determined.

As a control experiment, 100 μL of physiological saline in lieu of the adsorbent was taken in a vial, the same treatment as above was carried out, and the immune complex concentration in the solution was determined.

The adsorption ratio of an immune complex (%) was calculated by the following formulas. The results are shown in Table 4.

Adsorption ratio (%)={(V3r−V3t/V3r)}×100

V3r: The immune complex concentration in a control experiment solution

V3t: The immune complex concentration in an adsorption experiment supernatant

TABLE 4

| | Adsorbent | Adsorption ratio of an immune complex before sterilization (%) | Adsorption ratio of an immune complex after sterilization (%) |
|---|---|---|---|
| Example 2 | Sephacryl S1000-B04 | 92.4 | 91.6 |
| Example 4 | Sepharose 4B-C15 | 85.2 | 84.1 |
| Example 5 | TOYOPEARL-C24 | 81.5 | 80.5 |

EXAMPLE 11

Evaluation of the IgG Adsorption Capacity of the Synthesized Adsorbents

Sephadex G-150 (product of Amersham Pharmacia Biotech: exclusion limit of molecular weight for spherical protein; ca 300,000), which is a dextran beady gel, was epoxidated in the same manner as in Example 1 to synthesize an adsorbent Sephadex G-150-C36 by immobilizing C36 peptide on the gel. The radiation sterilization of 0.5 mL each of the adsorbent Sephadex G-150-C36 and the adsorbent G-150, on which a peptide is not immobilized, with cobalt 60 γ rays (25 KGy, 3 hrs.) was commissioned to Koga Isotope Co., Ltd.

An adsorption experiment was carried out in the same manner as in Example 7. The results are shown in Table 5.

TABLE 5

| | Adsorbent | Adsorption ratio of IgG (%) |
| --- | --- | --- |
| Example 11 | Sephadex G-150-C36 | 59.7 |
| (Control) | Sephadex G-150 | 2.1 |

INDUSTRIAL APPLICABILITY

As is clear from the above description, the present invention provides a novel peptide having capacity for selective adsorption of an immunoglobulin and/or an immune complex present in a body fluid, a recombinant DNA for synthesizing said peptide, a microorganism comprising the DNA, and a novel adsorbent produced by the above peptide. Furthermore, it becomes possible to selectively remove an immunoglobulin and/or an immune complex in a tested solution, such as blood, plasma and serum, to be treated by using body fluid treating equipment which is filled with said adsorbent.

The invention claimed is:

1. An adsorbent for an immunoglobulin and/or immune complex, the adsorbent comprising a water-insoluble carrier and a peptide immobilized thereon, wherein said peptide consists of the amino acid sequence of SEQ ID NO:10.

2. An adsorbent for an immunoglobulin and/or immune complex, the adsorbent comprising a water-insoluble carrier and a peptide immobilized thereon, wherein said peptide consists of the amino acid sequence of SEQ ID NO:11.

3. An adsorbent for an immunoglobulin and/or immune complex, the adsorbent comprising a water-insoluble carrier and a peptide immobilized thereon, wherein said peptide consists of the amino acid sequence of SEQ ID NO:13.

4. An adsorbent for an immunoglobulin and/or immune complex, the adsorbent comprising a water-insoluble carrier and a peptide immobilized thereon, wherein said peptide consists of the amino acid sequence of SEQ ID NO:15.

5. The adsorbent for an immunoglobulin and/or an immune complex according to any one of claims 1–4, wherein the water-insoluble carrier is porous.

6. The adsorbent for an immunoglobulin and/or an immune complex according to any one of claims 1–4, wherein the water-insoluble carrier is hydrophilic one.

7. The adsorbent for an immunoglobulin and/or an immune complex according to claim 5, wherein the exclusion limit of molecular weight of the water-insoluble carrier is not less than 150,000.

8. An adsorption unit which comprises the absorbent according to any one of claims 1–4, filled in a container having a liquid inlet and a liquid outlet and equipped with at least one filter.

* * * * *

UNITED STATES PATENT AND TRADEMARK OFFICE
CERTIFICATE OF CORRECTION

| | |
|---|---|
| PATENT NO. | : 7,153,945 B2 |
| APPLICATION NO. | : 10/489202 |
| DATED | : December 26, 2006 |
| INVENTOR(S) | : Eiji Ogino et al. |

It is certified that error appears in the above-identified patent and that said Letters Patent is hereby corrected as shown below:

Column 32, line 62, replace "absorbent" with --adsorbent--.

Signed and Sealed this

First Day of May, 2007

JON W. DUDAS
*Director of the United States Patent and Trademark Office*